United States Patent [19]
Buckland et al.

[11] Patent Number: 6,110,927
[45] Date of Patent: Aug. 29, 2000

[54] LORATADINE FOR USE AS AN ANTIARRHYTHMIC

[75] Inventors: Guy Buckland, Cos Cob; Tilman Friedrich, Groton Long Point, both of Conn.; Carol A. Satler, Boston, Mass.

[73] Assignee: Pfizer Inc, New York, N.Y.

[21] Appl. No.: 09/342,007

[22] Filed: Jun. 28, 1999

Related U.S. Application Data

[60] Provisional application No. 60/091,246, Jun. 30, 1998.

[51] Int. Cl.⁷ .................................................. A61K 31/44
[52] U.S. Cl. .............................................................. 514/290
[58] Field of Search ................................................. 514/290

[56] References Cited

U.S. PATENT DOCUMENTS

| | | | |
|---|---|---|---|
| 4,282,233 | 8/1981 | Vilani | 424/267 |
| 4,371,516 | 2/1983 | Gregory et al. | 424/22 |
| 4,659,716 | 4/1987 | Villani et al. | 514/290 |

OTHER PUBLICATIONS

Mays et al., J. Clin. Invest., 96:282–92 (1995).
Radwanski et al., J. Clin. Pharmacol., 27:530–33 (1987).
Hey et al., Clin. Exp. Allergy, 25:974–84 (1995).
Luck et al., J. Allergy Clin. Immunol. (Abstract), 282:568 (1995).
[author?], Am. J. Cardiol., 74:208 (1994).
Delpon et al., Cardiovasc. Res., 35:341–50 (1997).
Haria et al., Drugs, 48(4):617–37 (1994).

*Primary Examiner*—Raymond Henley, III
*Attorney, Agent, or Firm*—Peter C. Richardson; Gregg C. Benson; Gregory P. Raymer

[57] ABSTRACT

A method of treating atrial fibrillation in mammals using loratadine.

11 Claims, No Drawings

LORATADINE FOR USE AS AN ANTIARRHYTHMIC

This application is filed claiming priority from co-pending Provisional Application No. 60/091,246 filed Jun. 30, 1998.

BACKGROUND OF INVENTION

This invention relates to the use of loratadine to treat arrhythmias including atrial fibrillation in mammals.

Estimates for the prevalence of atrial fibrillation (AF) in the US range from 2.2–3 million patients. It is commonly a disease of the elderly (affecting 13% of 70–80 year olds) and is therefore expected to increase as a result of changing demographics. AF is responsible for ⅓ of all strokes in people over 65 years, and has associated costs of approximately $9 billion/year. Current therapy is to allow patients to remain in AF and reduce the ventricular rate by pharmacological means. This is considered safe, although it is believed that there are significant benefits of being in sinus rhythm (vs. rate control).

There are some new therapies for the treatment of arrhythmias under examination. For example, dofetilide is a selective inhibitor of the rapid component of the delayed rectifier potassium current which prolongs the action potential duration and the effective refractory period in a concentration dependent manner. Clinical studies have demonstrated that dofetilide is effective in treating patients with atrial arrhythmias.

There is also ongoing research related to the Kv 1.5 channel blockers. Regulation of the resting membrane potential and action potential duration of the heart is mediated by four principal K+ currents: an inwardly rectifying current ($I_{K1}$), a transient outward current ($I_{To}$) and rapid ($I_{Kr}$) and slow ($I_{Ks}$) delayed rectifying currents. At the molecular level, recent studies have shown $I_{K1}$ may be produced by at least 3 genes from the Kir family, while the remaining currents are mediated by members of the voltage-dependent potassium channel (Kv) superfamily.

The Kv1.5 channel produces a current identical to the ultrarapid outwardly rectifying K+ current ($I_{Kur}$) identified in the atria. Inhibitors of the Kv1.5 channel have been shown to prolong action potential in the human atrial myocytes Fedida D. Et al. Circ Res 1993;73:210–216.

Delpon, Eva, et al., in Cardiovascular Research 35 (1997) 341–350 discloses that loratadine blocked hKv1.5 channels in a concentration-, voltage-, time- and use-dependent manner but only at concentrations much higher than therapeutic plasma levels in man. This would indicate the possibility of antiarrhythmic properties for this compound. However, the use of loratadine for such indication is only a possibility since, for example, there have been at least 2 reported cases of atrial fibrillation in the literature with loratadine use both with and without a history of similar arrhythmia (Good A P Am J. Cardiol 1994;Jul. 15;74(2):208–9 and Luck J et al J allergy Clin Immunol 1995;95:282). This opens up the possibility that loratadine, although having properties which may prevent atrial arrhythmia, may also have the potential for initiating this arrhythmia.

Although there are some therapies for the treatment of atrial fibrillation there is a continuing search in this field of art for new therapies.

SUMMARY OF THE INVENTION

This invention is directed to a method for treating arrhythmias, including atrial fibrillation, in a mammal comprising administering to a mammal (e.g., humans either male or female) in need of treatment thereof a therapeutically effective amount of loratadine, metabolites thereof or pharmaceutically acceptable salts of loratadine or metabolites thereof.

A preferred method is wherein the compound is loratadine.

A preferred amount of loratadine is about 0.5 mg/kg/day to about 10 mg/kg/day, preferably about 1.5 mg/kg/day to about 4.5 mg/kg/day.

Another preferred aspect of this invention is wherein the compound is descarboethoxyloratadine.

A preferred amount of descarboethoxyloratadine is about 0.1 mg/kg/day to about 100 mg/kg/day.

A preferred method is wherein atrial fibrillation is treated.

It is especially preferred that maintenance of normal sinus rhythm is improved.

A particularly preferred mammal is a female or male human.

The term arrhythmia refers to conditions in which the normal rhythm of the heart, particularly the sinus rhythm varies.

The term "treating", "treat" or "treatment" as used herein includes preventative (e.g., prophylactic) and palliative treatment.

By "pharmaceutically acceptable" it is meant the carrier, diluent, excipients, and/or salt must be compatible with the other ingredients of the formulation, and not deleterious to the recipient thereof.

The expression "pharmaceutically-acceptable salt" refers to nontoxic anionic salts containing anions such as (but not limited to) chloride, bromide, iodide, sulfate, bisulfate, phosphate, acetate, maleate, fumarate, oxalate, lactate, tartrate, citrate, gluconate, methanesulfonate and 4-toluenesulfonate.

Hydrates and solvents of the compounds of this invention are also included.

Other features and advantages will be apparent from the specification and claims which describe the invention.

DETAILED DESCRIPTION OF THE INVENTION

Loratadine is named as ethyl 4-(8-chloro-5,6-dihydro-11-H-benzo [5,6] cyclohepta-[1,2-b]-pyridin-11-ylidene)-1-piperidinecarboxylate and has the chemical Formula I

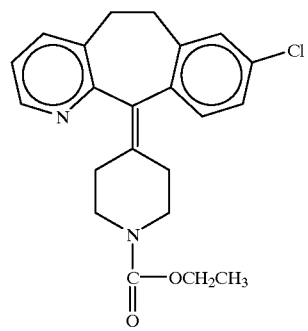

Formula I

One active metabolite of loratadine is known as descarboethoxyloratadine and has the chemical Formula II. The metabolite may be prepared by removal of the carboethoxy moety according to methods known to those skilled in the art.

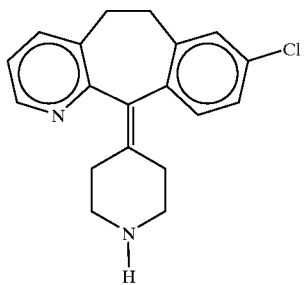

Formula II

Loratadine and methods for making loratadine are disclosed in U.S. Pat. No. 4,282,233, the disclosure of which is hereby incorporated by reference. The pharmacokinetics of loratadine is discussed in J. Clin. Pharmacol. 1987;27:530–533 and J. Clin. Pharmacol. 1987;27:694–698.

The starting materials and reagents for the above described compounds, are also readily available or can be easily synthesized by those skilled in the art using conventional methods of organic synthesis.

Loratadine and descarboethoxyloratadine are basic and they form salts with pharmaceutically acceptable anions. All such salts are within the scope of this invention and they can be prepared by conventional methods. For example, they can be prepared simply by contacting the acidic and basic entities, usually in a stoichiometric ratio, in either an aqueous, non-aqueous or partially aqueous medium, as appropriate. The salts are recovered either by filtration, by precipitation with a non-solvent followed by filtration, by evaporation of the solvent, or, in the case of aqueous solutions, by lyophilization, as appropriate.

The utility of the compounds of the present invention in the treatment of arrhythmias such as atrial fibrillation in mammals (e.g. humans) is demonstrated by the activity of the compounds of this invention in conventional assays and the clinical protocol described below. Such assays and clinical protocol also provide a means whereby the activities of the compounds of this invention can be compared with the activities of other known compounds. The results of these comparisons are useful for determining dosage levels in mammals, including humans, for the treatment of such diseases.

The anti-arrhythmic activity of the compounds of this invention can be determined utilizing the following assay.

ASSAY

For assessment of effects of the compounds on atrial refractoriness, guinea pig right hemiatria are mounted in a bath containing physiological salt solution, and one end is connected to a force transducer. Tissues are stimulated at 1 Hz using field electrodes. Effective refractory period (ERP) is measured by introducing premature stimuli ($S_2$) after every 8th basic stimulus ($S_1$). The $S_1S_2$ coupling interval is gradually increased until S2 reproducibly elicits a propagated response. This is defined as the ERP. The concentration of compound required to increase ERP by 25% ($ED_{25}$) is then determined. ERP is also measured in guinea pig right papillary muscles incubated in physiological salt solution. Muscles are stimulated at one end using bipolar electrodes and the propagated electrogram is recorded at the opposite end via a unipolar surface electrode. ERP is determined as above using the extrastimulus technique. Condition time is obtained from a digital storage oscilloscope by measuring the interval between the stimulus artifact and the peak of the electrogram (i.e., the time required for the impulse to travel along the length of the muscle).

Atrial and ventricular ERP's are also measured in anaesthetized or conscious dogs by the extrastimulus technique whilst the atrium or right ventricle is being paced at a constant rate.

For assessment of effects of the test compound on atrial refractoriness in humans, the following protocol is performed:

ELECTROPHYSIOLOGICAL STUDY PROTOCOL

The patient is brought to the Clinical Electrophysiology Laboratory in the fasting state. Small doses of intravenous benzodiazepines are permitted for sedation at the discretion of the investigator. Quadripolar or tripolar catheters are inserted via the brachial or femoral veins and advanced under fluoroscopic control into the high right atrium, across the tricuspid valve and into the right ventricle. A quadripolar catheter is introduced into the high right atrium and a tripolar catheter is placed across the tricuspid valve to record the His bundle potential. Another catheter is introduced and advanced to the right ventricular apex. Conduction parameters is determined by use of standard methods; refractory periods in the relevant tissues is determined by use of the extrastimulus technique. Sinus node recovery time is measured following a period of 90 sec continuous atrial pacing at cycle length of 600 and 450 msec. The longest RR interval in the first 5 sec after the end of pacing is measured. The following parameters are determined immediately prior to dosing and in the middle of the maintenance infusion:

Conduction parameters: PA, AH, HV, PR and QRS intervals.
    The wenckebach point is also be determined.
Refractoriness: The effective and functional refractory periods in the atria, ventricles, AV node and His-Purkinje system are determined. Refractory periods are determined at cycle length of 600 and 450 msec.
Sinus node: Sinus Node Recovery Time (SNRT); Corrected Sinus Node Recovery Time
    (SNRTcor); Sinus Cycle Length; Sino-Atrial Conduction Time (SACT); Corrected sino atrial conduction time (SACTcor).
Repolarization parameters: QT and QTc intervals; JT and JTc intervals.

Administration of the compounds of this invention can be via any method which delivers the compound, preferentially to the desired tissue (e.g., cardiac tissues). These methods include oral routes, parenteral, intraduodenal routes, etc. Generally, the compounds of the present invention are administered in single (e.g., once daily) or multiple doses.

The compounds of this invention are useful in treating arrhythmias such as atrial fibrillation and maintaining normal sinus rhythm. Thus, the compounds of this invention are useful for improving sinus rhythm in patients at risk for a recurrence of atrial fibrillation post cardioversion.

Generally, the compounds of this invention are administered orally, but parenteral administration (e.g., intravenous, intramuscular, subcutaneous or intramedullary) may be utilized, for example, where oral administration is inappropriate for the instant target or where the patient is unable to ingest the drug. Topical administration may also be indicated, for example, where the patient is suffering from gastrointestinal disorders or whenever the medication is best applied to the surface of a tissue or organ as determined by the attending physician.

In any event the amount and timing of the compound administered will, of course, be dependent on the subject being treated, on the severity of the affliction, on the manner of administration and on the judgment of the prescribing physician. Thus, because of patient to patient variability, the dosages given below are a guideline and the physician may titrate doses of the compounds to achieve the treatment (e.g., antiarrhythmic effect) that the physician considers appropriate for the patient. In considering the degree of treatment desired, the physician must balance a variety of factors such as age of the patient, presence of preexisting disease, as well as presence of other diseases (e.g., congestive heart failure).

The compound of this invention is typically administered in a chronic daily mode.

An amount of the compounds of this invention that is effective for the activities of this invention, for example the, antiarrhythmic activities is used.

In general an effective dosage for the activities of this invention, for example the antiarrhythmic activities of loratadine, is in the range of about 0.5 mg/kg/day to about 10 mg/kg/day, preferably about 1.5 mg/kg/day to about 4.5 mg/kg/day based on a 70 kg individual.

In general an effective dosage for the activities of this invention, for example the antiarrhythmic activities of descarboethoxyloratadine and other metabolites is in the range of about 0.1 mg/kg/day to about 100 mg/kg/day based on a 70 kg individual.

The compounds of the present invention are generally administered in the form of a pharmaceutical composition comprising the active ingredient together with a pharmaceutically acceptable vehicle or diluent.

For oral administration a pharmaceutical composition can take the form of solutions, suspensions, tablets, pills, capsules, powders, and the like. Tablets containing various excipients such as sodium citrate, calcium carbonate and calcium phosphate are employed along with various disintegrants such as starch and preferably potato or tapioca starch and certain complex silicates, together with binding agents such as polyvinylpyrrolidone, sucrose, gelatin and acacia. Additionally, lubricating agents such as magnesium stearate, sodium lauryl sulfate and talc are often very useful for tabletting purposes. Solid compositions of a similar type are also employed as fillers in soft and hard-filled gelatin capsules; preferred materials in this connection also include lactose or milk sugar as well as high molecular weight polyethylene glycols. When aqueous suspensions and/or elixirs are desired for oral administration, the compounds of this invention can be combined with various sweetening agents, flavoring agents, coloring agents, emulsifying agents and/or suspending agents, as well as such diluents as water, ethanol, propylene glycol, glycerin and various like combinations thereof.

For purposes of parenteral administration, solutions in sesame or peanut oil or in aqueous propylene glycol can be employed, as well as sterile aqueous solutions of the corresponding water-soluble salts. Such aqueous solutions may be suitably buffered, if necessary, and the liquid diluent first rendered isotonic with sufficient saline or glucose. These aqueous solutions are especially suitable for intravenous, intramuscular, subcutaneous and intraperitoneal injection purposes. In this connection, the sterile aqueous media employed are all readily obtainable by standard techniques well-known to those skilled in the art.

For purposes of transdermal (e.g., topical) administration, dilute sterile, aqueous or partially aqueous solutions (usually in about 0.1% to 5% concentration), otherwise similar to the above parenteral solutions, are prepared.

Methods of preparing various pharmaceutical compositions with a certain amount of active ingredient are known, or will be apparent in light of this disclosure, to those skilled in this art. For examples of methods of preparing pharmaceutical compositions, see *Remington's Pharmaceutical Sciences*, Mack Publishing Company, Easter, Pa., 15th Edition (1975).

Pharmaceutical compositions according to this invention may contain 0.1%–95% of the compound(s) of this invention, preferably 1%–70%. In any event, the composition or formulation to be administered will contain a quantity of a compound(s) according to the invention in an amount effective to treat the disease/condition of the subject being treated.

The compounds of this invention either alone or in combination with each other or other compounds generally will be administered in a convenient formulation. The following formulation examples only are illustrative and are not intended to limit the scope of the present invention.

In the formulations which follow, "active ingredient" means compound(s) of this invention.

Formulation 1: Gelatin Capsules
Hard gelatin capsules are prepared using the following:

| Ingredient | Quantity (mg/capsule) |
| --- | --- |
| Active ingredient | 0.25–100 |
| Starch, NF | 0–650 |
| Starch flowable powder | 0–50 |
| Silicone fluid 350 centistokes | 0–15 |

A tablet formulation is prepared using the ingredients below:

Formulation 2: Tablets

| Ingredient | Quantity (mg/tablet) |
| --- | --- |
| Active ingredient | 0.25–100 |
| Cellulose, microcrystalline | 200–650 |
| Silicon dioxide, fumed | 10–650 |
| Stearate acid | 5–15 |

The components are blended and compressed to form tablets.

Alternatively, tablets each containing 0.25–100 mg of active ingredient are made up as follows:

Formulation 3: Tablets

| Ingredient | Quantity (mg/tablet) |
| --- | --- |
| Active ingredient | 0.25–100 |
| Starch | 45 |
| Cellulose, microcrystalline | 35 |
| Polyvinylpyrrolidone (as 10% solution in water) | 4 |
| Sodium carboxymethyl cellulose | 4.5 |
| Magnesium stearate | 0.5 |
| Talc | 1 |

The active ingredient, starch, and cellulose are passed through a No. 45 mesh U.S. sieve and mixed thoroughly. The solution of polyvinylpyrrolidone is mixed with the resultant powders which are then passed through a No. 14 mesh U.S. sieve. The granules so produced are dried at 50°–60° C. and passed through a No. 18 mesh U.S. sieve. The sodium carboxymethyl starch, magnesium stearate, and talc, previously passed through a No. 60 U.S. sieve, are then added to the granules which, after mixing, are compressed on a tablet machine to yield tablets.

Suspensions each containing 0.25–100 mg of active ingredient per 5 ml dose are made as follows:

Formulation 4: Suspensions

| Ingredient | Quantity (mg/5 ml) |
|---|---|
| Active ingredient | 0.25–100 mg |
| Sodium carboxymethyl cellulose | 50 mg |
| Syrup | 1.25 mg |
| Benzoic acid solution | 0.10 mL |
| Flavor | q.v. |
| Color | q.v. |
| Purified Water to | 5 mL |

The active ingredient is passed through a No. 45 mesh U.S. sieve and mixed with the sodium carboxymethyl cellulose and syrup to form smooth paste. The benzoic acid solution, flavor, and color are diluted with some of the water and added, with stirring. Sufficient water is then added to produce the required volume.

An aerosol solution is prepared containing the following ingredients:

Formulation 5: Aerosol

| Ingredient | Quantity (% by weight) |
|---|---|
| Active ingredient | 0.25 |
| Ethanol | 25.75 |
| Propellant 22 (Chlorodifluoromethane) | 70.00 |

The active ingredient is mixed with ethanol and the mixture added to a portion of the propellant 22, cooled to 30° C., and transferred to a filling device. The required amount is then fed to a stainless steel container and diluted with the remaining propellant. The valve units are then fitted to the container.

Suppositories are prepared as follows:

Formulation 6: Suppositories

| Ingredient | Quantity (mg/suppository) |
|---|---|
| Active ingredient | 250 |
| Saturated fatty acid glycerides | 2,000 |

The active ingredient is passed through a No. 60 mesh U.S. sieve and suspended in the saturated fatty acid glycerides previously melted using the minimal necessary heat. The mixture is then poured into a suppository mold of nominal 2 g capacity and allowed to cool.

An intravenous formulation is prepared as follows:

Formulation 7: Intravenous Solution

| Ingredient | Quantity |
|---|---|
| Active ingredient | 20 mg |
| Isotonic saline | 1,000 mL |

The solution of the above ingredients is intravenously administered to a patient at a rate of about 1 mL per minute.

What is claimed is:

1. A method for treating an arrhythmia in a mammal, said method comprising administering to said mammal a therapeutically effective amount of loratadine, metabolites thereof or a pharmaceutically acceptable salt of loratadine or said metabolites.

2. A method as recited in claim 1 wherein the compound is loratadine.

3. A method as recited in claim 2 wherein the amount of loratadine is about 1.5 mg/kg/day to about 4.5 mg/kg/day.

4. A method as recited in claim 2 wherein atrial fibrillation is treated.

5. A method as recited in claim 2 wherein normal sinus rhythm is maintained.

6. A method as recited in claim 4 wherein the mammal is a female or male human.

7. A method as recited in claim 1 wherein the compound is descarboethoxyloratadine.

8. A method as recited in claim 7 wherein the amount of descarboethoxyloratadine is about 0.1 mg/kg/day to about 100 mg/kg/day.

9. A method as recited in claim 7 wherein atrial fibrillation is treated.

10. A method as recited in claim 7 wherein normal sinus rhythm is maintained.

11. A method as recited in claim 9 wherein the mammal is a female or male human.

* * * * *